(12) United States Patent
Shi et al.

(10) Patent No.: US 12,090,156 B2
(45) Date of Patent: Sep. 17, 2024

(54) APPLICATION OF CB-839 IN PREPARATION OF DRUG FOR INHIBITING CORNEAL NEOVASCULARIZATION (CNV)

(71) Applicant: Institute of Ophthalmology Affiliated to Shandong First Medical University (Shandong Institute of, Qingdao (CN)

(72) Inventors: Weiyun Shi, Qingdao (CN); Qingjun Zhou, Qingdao (CN); Hongwei Wang, Qingdao (CN); Bining Zhang, Qingdao (CN)

(73) Assignee: INSTITUTE OF OPHTHALMOLOGY AFFILIATED TO SHANDONG FIRST MEDICAL UNIVERSITY (SHANDONG INSTITUTE OF OPHTHALMO, Qingdao (CN)

(*) Notice: Subject to any disclaimer, the term of this patent is extended or adjusted under 35 U.S.C. 154(b) by 0 days.

(21) Appl. No.: 18/573,439

(22) PCT Filed: Feb. 15, 2023

(86) PCT No.: PCT/CN2023/076103
§ 371 (c)(1),
(2) Date: Dec. 22, 2023

(87) PCT Pub. No.: WO2023/169163
PCT Pub. Date: Sep. 14, 2023

(65) Prior Publication Data
US 2024/0261281 A1    Aug. 8, 2024

(30) Foreign Application Priority Data
Mar. 9, 2022 (CN) .................. 202210233115.X

(51) Int. Cl.
| | | |
|---|---|---|
| *A61K 31/501* | (2006.01) |
| *A61K 9/06* | (2006.01) |
| *A61K 9/127* | (2006.01) |
| *A61K 47/24* | (2006.01) |
| *A61K 47/28* | (2006.01) |
| *A61K 47/42* | (2017.01) |
| *A61P 27/02* | (2006.01) |

(52) U.S. Cl.
CPC .............. *A61K 31/501* (2013.01); *A61K 9/06* (2013.01); *A61K 9/127* (2013.01); *A61K 47/24* (2013.01); *A61K 47/28* (2013.01); *A61K 47/42* (2013.01); *A61P 27/02* (2018.01)

(58) Field of Classification Search
CPC ........ A61K 31/501; A61K 9/06; A61K 9/127; A61K 47/24; A61K 47/28; A61K 47/42
USPC ...................................... 514/252.03
See application file for complete search history.

(56) References Cited

FOREIGN PATENT DOCUMENTS

| | | | | |
|---|---|---|---|---|
| CN | 107714650 A | 2/2018 | | |
| CN | 114917230 A | 8/2022 | | |
| WO | WO-2019104038 A1 * | 5/2019 | ........... A61K 31/409 |
| WO | 2022001784 A1 | 1/2022 | | |
| WO | 2022251370 A1 | 12/2022 | | |

OTHER PUBLICATIONS

Hongling Huang, et al., Role of glutamine and interlinked asparagine metabolism in vessel formation, The Embo Journal, 2017, pp. 2334-2352, vol. 36 No. 16.

* cited by examiner

*Primary Examiner* — Yevgeny Valenrod
(74) *Attorney, Agent, or Firm* — Bayramoglu Law Offices LLC

(57) ABSTRACT

In view of the problem that the current prevention and treatment manners for corneal neovascularization (CNV) may cause complications, the present disclosure provides an application of CB-839 in preparation of a drug for inhibiting CNV. The CB-839-loaded drug of the present disclosure can significantly inhibit CNV in mice and reduce the infiltration of inflammatory cells without obvious side effects, which makes up for the shortcoming of the prior art.

11 Claims, 1 Drawing Sheet

Alkali-burned model

Control group

CB-839

APPLICATION OF CB-839 IN PREPARATION OF DRUG FOR INHIBITING CORNEAL NEOVASCULARIZATION (CNV)

CROSS REFERENCE TO THE RELATED APPLICATIONS

This application is the national phase entry of International Application No. PCT/CN2023/076103, filed on Feb. 15, 2023, which is based upon and claims priority to Chinese Patent Application No. 202210233115.X, filed on Mar. 9, 2022, the entire contents of which are incorporated herein by reference.

TECHNICAL FIELD

The present disclosure belongs to the technical field of preparation of ophthalmic drugs, and specifically relates to an application of CB-839 in preparation of a drug for inhibiting corneal neovascularization (CNV).

BACKGROUND

The prevention and treatment of CNV is a major clinical challenge. When a cornea is affected by internal and external factors such as injury, infection, corneal operations, and genetic diseases, an excessive oxidative stress will occur in the cornea to trigger the up-regulation of pro-angiogenic factors, which causes the invasion of capillaries from a corneoscleral limbus to the cornea to produce CNV, resulting in vision loss in a patient and even blindness in severe cases.

Currently, clinical pharmaceutical and surgical prevention and treatment manners are often accompanied by complications such as glaucoma, cataract, corneal epithelial injury, or corneal superinfection. Therefore, it is urgent and necessary to develop a novel technology for preventing CNV.

SUMMARY

In view of the above-mentioned problem that the current prevention and treatment manners for CNV may cause complications, the present disclosure provides an application of CB-839 in preparation of a drug for inhibiting CNV. The CB-839-loaded drug can significantly inhibit CNV in mice without complications, which makes up for the shortcoming of the prior art.

The present disclosure is implemented by the following technical solutions:

An application of CB-839 in preparation of a drug for inhibiting CNV is provided.

CB-839 is a non-competitive selective inhibitor for glutaminase 1 (GLS1), which exhibits a significant antiproliferative activity for cancer cell lines such as triple-negative breast cancer (TNBC), lung adenocarcinoma, chondrosarcoma, and lymphoma cell lines.

Further, the CNV is produced due to invasion of capillaries from a corneoscleral limbus to a cornea when an excessive oxidative stress occurs in the cornea to trigger up-regulation of pro-angiogenic factors.

Further, a dosage form of the drug for inhibiting CNV is a sustained-release hydrogel, a liposome, or a polylactic acid-hydroxyacetic acid copolymer microsphere.

Further, the sustained-release hydrogel refers to a hydrogel-based sustained-release agent, and a preparation method of the hydrogel-based sustained-release agent includes the following steps: thoroughly mixing gelatin with the CB-839 to obtain an aqueous solution, adding carboxymethyl cellulose (CMC) and an N-hydroxysulfosuccinimide sodium salt to the aqueous solution, thoroughly mixing a resulting mixture, and allowing the mixture to stand at room temperature to obtain the hydrogel-based sustained-release agent loaded with the CB-839.

Further, in the aqueous solution prepared by thoroughly mixing the gelatin with the CB-839, a concentration of the gelatin is 0.03 mg/mL to 0.08 mg/mL and a concentration of the CB-839 is 0.3 mg/mL to 0.5 mg/mL.

Further, in the aqueous solution prepared by thoroughly mixing the gelatin with the CB-839, the concentration of the gelatin is 0.05 mg/mL and the concentration of the CB-839 is 0.4 mg/mL.

Further, the liposome refers to a liposome-based sustained-release agent, and a preparation method of the liposome-based sustained-release agent includes the following steps: dispersing soybean lecithin, cholesterol, and the CB-839 jointly in dichloromethane (DCM) to obtain a homogeneous solution, and subjecting the homogeneous solution to evaporation under reduced pressure to dryness; dispersing a residue in water, centrifuging a resulting dispersion, and discarding a resulting supernatant; and adding water to a resulting precipitate, and thoroughly mixing a resulting mixture to obtain the liposome-based sustained-release agent loaded with the CB-839.

Further, the dispersing refers to ultrasonic dispersion.

Beneficial effects of the present disclosure: The drug obtained in the present disclosure can effectively inhibit CNV and thus can be used for a continuous treatment of CNV. The present disclosure overcomes the shortcomings of poor solubility and low bioavailability of CB-839, can reduce the inconvenience caused by multiple and frequent use of traditional preparations, and makes the drug exert an efficient and long-lasting therapeutic effect.

DETAILED DESCRIPTION OF THE EMBODIMENTS

Figure 1A:
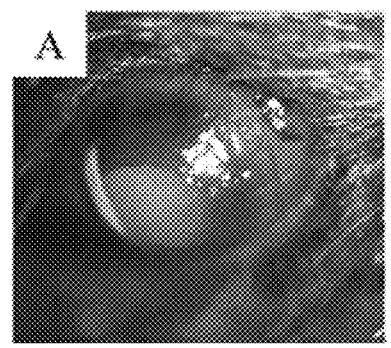
FIGS. 1A-1D show images of eyes of mice in an animal experiment.

The present disclosure is further described in detail below with reference to specific examples.

Example 1: Preparation of a Hydrogel-Based Sustained-Release Material Loaded with CB-839

(1) 50 mg of gelatin and 2 mg of CB-839 were added to a centrifuge tube.
(2) 1 mL of water was added to the centrifuge tube after step (1).
(3) A resulting mixed system was ultrasonically treated at room temperature for 20 min to allow complete dissolution to obtain a homogeneous solution.
(4) 4.5 mg of CMC and 1.8 mg of an N-hydroxysulfosuccinimide sodium salt were added as a catalyst to the centrifuge tube after step (3).
(5) The centrifuge tube with a mixed solution obtained in step (4) was placed at room temperature for 1 h to obtain the hydrogel-based sustained-release material loaded with CB-839.

Example 2: Preparation of a Liposome-Based Sustained-Release Material Loaded with CB-839

(1) 60 mg of soybean lecithin, 16 mg of cholesterol, and 4 mg of CB-839 were added to a round-bottom flask.

(2) 20 mL of DCM was added to the round-bottom flask after step (1).

(3) A resulting mixed system was ultrasonically treated at room temperature for 20 min to allow complete dissolution to obtain a homogeneous solution.

(4) The homogeneous solution obtained in step (3) was subjected to slow evaporation under reduced pressure to dryness.

(5) 20 mL of water was added to the round-bottom flask after step (4), and hydration was conducted for 1 h.

(6) A solution obtained in step (5) was ultrasonically treated for 2 min.

(7) A system obtained in step (6) was centrifuged at 6,000 rpm for 5 min, and a resulting supernatant was discarded.

(8) 10 mL of water was added to a precipitate obtained in step (7), and a resulting mixture was thoroughly mixed to obtain the liposome-based sustained-release material loaded with CB-839.

Animal Experiment

1. Establishment of an Alkali-Burned Animal Model (1) A round filter paper with a diameter of about 2 mm was soaked in a 1 mol/L NaOH Solution (2) Balb/c mice were anesthetized by injecting pentobarbital sodium at 90 mg/kg, where 0.3 mL of a pentobarbital sodium solution was injected per 25 g of mice or 1.8 mg of pentobarbital sodium was injected per 25 g of mice. An anesthetic action started 1 min to 2 min after the injection of pentobarbital sodium. An anesthetic depth could be determined by gently pinching a toe or tail of an animal, and if the anesthetic depth was sufficient, there should be no response.

(3) A 0.5% proparacaine hydrochloride ophthalmic solution was applied to a corneal surface of each mouse for local analgesia.

(4) A NaOH-soaked filter paper was picked up with sterile forceps. If excess sodium hydroxide adhered to or dropped down from the filter paper, the soaked filter paper was gently patted with a dry filter paper to absorb the excess sodium hydroxide. The sodium hydroxide-soaked filter paper was placed in a center of a cornea for 40 s to produce an acute alkali burn with an area of about 2×2 $mm^2$.

(5) The soaked filter paper was removed. A 10 mL syringe was used to gently rinse an eye with 10 mL of 0.9% normal saline (NS) for 40 s to remove the residual 1 mol/L NaOH.

(6) An incision of about 1 mm was gently formed under a conjunctiva of each mouse in an experimental group, then about 0.05 mg of the hydrogel-based sustained-release material loaded with CB-839 (Example 1) was implanted under the conjunctiva with sterile forceps, and the incision was sutured with an 11-0 Mani suture. Mice in a control group were not treated.

Figure 1B:
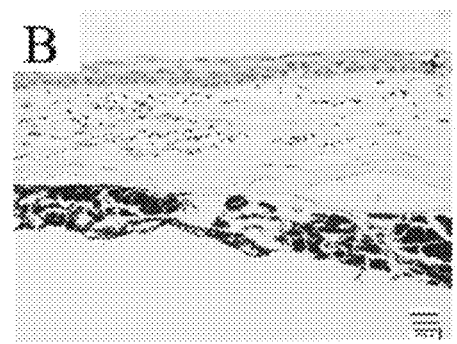
Figure 1C:
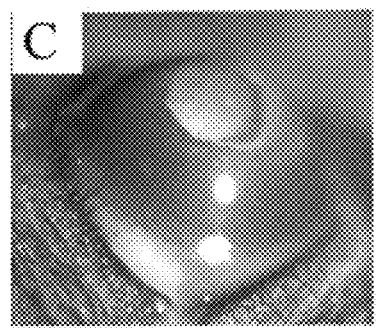
Figure 1D:
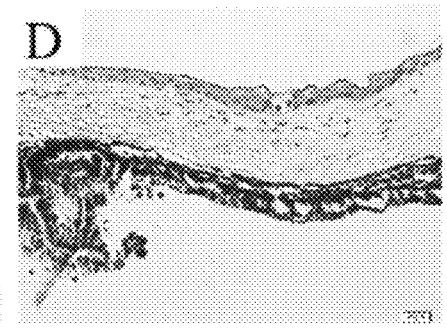

(7) A representative image of an eye was acquired on day 5 using a slit lamp for ophthalmic examination. FIGS. 1D-1D show images of eyes of mice in the experiment. Results show that mice in the control group have obvious blood vessels (FIG. 1A), while mice in the experimental group do not undergo obvious neovascularization (FIG. 1C), indicating that CB-839 is released by the hydrogel-based sustained-release material to inhibit CNV, which is manifested as the reduction of a CNV area and inflammatory cell infiltration in the mice of the experimental group (FIG. 1B and FIG. 1D) without significant side effects.

The above examples are only intended to describe the preferred implementations of the present disclosure, rather than to limit the scope of the present disclosure. Various alterations and improvements made by those of ordinary skill in the art based on the technical solution of the present disclosure without departing from the design spirit of the present disclosure shall fall within the protection scope of the appended claims of the present disclosure.

What is claimed is:

1. A method of preparing a hydrogel-based sustained-release agent loaded with CB-839 comprising the following steps:
    thoroughly mixing gelatin with CB-839 and water to obtain an aqueous solution,
    adding carboxymethyl cellulose and an N-hydroxysulfo-succinimide sodium salt to the aqueous solution to produce a resulting mixture,
    thoroughly mixing the resulting mixture, and
    allowing the resulting mixture to stand at room temperature to obtain the hydrogel-based sustained-release agent loaded with CB-839.

2. The method according to claim 1, wherein in the aqueous solution prepared by thoroughly mixing the gelatin with CB-839 and water, a concentration of the gelatin is 0.03 mg/mL to 0.08 mg/mL and a concentration of the CB-839 is 0.3 mg/mL to 0.5 mg/mL.

3. The application method according to claim 2, wherein the concentration of the gelatin is 0.05 mg/mL and the concentration of the CB-839 is 0.4 mg/mL.

4. A method of preparing a liposome-based sustained-release agent loaded with CB-839 comprising the following steps:
    dispersing soybean lecithin, cholesterol, and CB-839 together in dichloromethane to obtain a homogeneous solution, and subjecting the homogeneous solution to evaporation under reduced pressure to dryness to produce a residue;
    dispersing the residue in water to produce a resulting dispersion, centrifuging the resulting dispersion to produce a resulting supernatant and a resulting precipitate, and discarding the resulting supernatant; and adding water to the resulting precipitate to produce a resulting mixture, and thoroughly mixing the resulting mixture to obtain the liposome-based sustained-release agent loaded with CB-839.

5. The method according to claim 4, wherein the dispersing is done ultrasonically.

6. A hydrogel-based sustained-release agent loaded with CB-839 prepared according to the method of claim 1.

7. A method of inhibiting cornealneovascularization (CNV) in a patient in need of treatment comprising a step of administering the hydrogel-based sustained-release agent loaded with CB-839 according to claim 6 to the eye of the patient.

8. The method according to claim 7, wherein the CNV is caused by invasion of capillaries from a corneoscleral limbus to a cornea when an excessive oxidative stress occurs in the cornea to trigger up-regulation of pro-angiogenic factors.

9. A liposome-based sustained-release agent loaded with CB-839 prepared according to the method of claim 4.

10. A method of inhibiting cornealneovascularization (CNV) in a patient in need of treatment comprising a step of administering the liposome-based sustained-release agent loaded with CB-839 according to claim 9 to the eye of the patient.

11. The method according to claim 10, wherein the CNV is caused by invasion of capillaries from a corneoscleral limbus to a cornea when an excessive oxidative stress occurs in the cornea to trigger up-regulation of pro-angiogenic factors.

\* \* \* \* \*